United States Patent
Romero-Sarmiento et al.

(10) Patent No.: US 11,353,444 B2
(45) Date of Patent: Jun. 7, 2022

(54) SYSTEM AND METHOD FOR DETERMINING THE CHEMICAL COMPOSITION OF COMPOUNDS CONTAINED IN A SAMPLE

(71) Applicant: IFP Energies nouvelles, Rueil-Malmaison (FR)

(72) Inventors: Maria-Fernanda Romero-Sarmiento, Rueil-Malmaison (FR); Pierre Cadeau, Rueil-Malmaison (FR); Valerie Beaumont, Rueil-Malmaison (FR); Olivier Sissmann, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 100 days.

(21) Appl. No.: 16/920,991

(22) Filed: Jul. 6, 2020

(65) Prior Publication Data
US 2021/0003545 A1 Jan. 7, 2021

(30) Foreign Application Priority Data

Jul. 4, 2019 (FR) .................................. 19/07.457

(51) Int. Cl.
G01N 33/24 (2006.01)
G01N 33/28 (2006.01)
G01N 33/00 (2006.01)

(52) U.S. Cl.
CPC ....... G01N 33/241 (2013.01); G01N 33/2841 (2013.01); G01N 33/0047 (2013.01)

(58) Field of Classification Search
CPC .......................... G01N 33/241; G01N 33/2841
See application file for complete search history.

(56) References Cited

U.S. PATENT DOCUMENTS 3,953,171 A 4/1976 Espitalie et al.
4,325,907 A 4/1982 Dembicki, Jr. et al.
(Continued)

FOREIGN PATENT DOCUMENTS

EP 0691540 B1 2/2003
FR 2227797 A5 11/1974
(Continued)

OTHER PUBLICATIONS

Preliminary Search Report for FR 19/07.457, dated May 19, 2020 (2 pages).
(Continued)

Primary Examiner — John Fitzgerald
(74) Attorney, Agent, or Firm — Fitch, Even, Tabin & Flannery LLP

(57) ABSTRACT

The invention relates to a system and to a method for separating into at least one of liquid and gas phase compounds contained in a sample. The system comprises: an oven (D1) for heating in an inert atmosphere according to a sequence of temperatures, a first experimental setup (M1) connected to oven (D1) when it is in operation, comprising circulating the effluent resulting from heating in an inert atmosphere towards collection of (U) this effluent, a second experimental setup (M2) connected to first experimental setup (M1) when the oven is no longer in operation, comprising vacuum circulation (PI, P.G., TP) of the effluent collected by the first setup towards (T1, T2) which separate the collected effluent into at least one of liquid and gas phases.

15 Claims, 2 Drawing Sheets

(56) References Cited

U.S. PATENT DOCUMENTS

| | | | |
|---|---|---|---|
| 4,352,673 A | 10/1982 | Espitalie et al. | |
| 4,599,218 A * | 7/1986 | Demaison | G01N 1/2294 |
| | | | 422/89 |
| 4,904,604 A * | 2/1990 | Kivlen | G01N 33/2823 |
| | | | 436/139 |
| 5,843,787 A | 12/1998 | Trabelsi et al. | |
| 6,447,725 B1 * | 9/2002 | Inoue | G01N 33/1846 |
| | | | 422/78 |
| 6,497,844 B1 * | 12/2002 | Bacaud | G01N 31/10 |
| | | | 422/68.1 |
| 8,796,035 B2 * | 8/2014 | Espitalie | G01N 33/24 |
| | | | 436/160 |
| 10,088,465 B2 | 10/2018 | Pillot et al. | |
| 2016/0177711 A1 * | 6/2016 | Calleri | E21B 49/005 |
| | | | 73/152.04 |

FOREIGN PATENT DOCUMENTS

| | | |
|---|---|---|
| FR | 2 456 320 A1 | 12/1980 |
| FR | 2472754 A1 | 7/1981 |
| FR | 3021749 A1 | 12/2015 |
| GB | 2 271 179 A | 4/1994 |

OTHER PUBLICATIONS

Behar et al.; "Rock-Eval 6 Technology: Performances and Developments"; Oil & Gas Science and Technology—Rev. IFP, vol. 56(2001), No. 2, pp. 111-134 Copyright © 2001, Éditions Technip.
Doerner et al.; "Paleoenvironmental Characterization of Thermally Mature Organic Matter Using a New Pyrolysis—IRMS Method"; 28th International Meeting on Organic Geochemistry, Sep. 17-22, 2017, Florence, Italy.

* cited by examiner

[Fig 1]
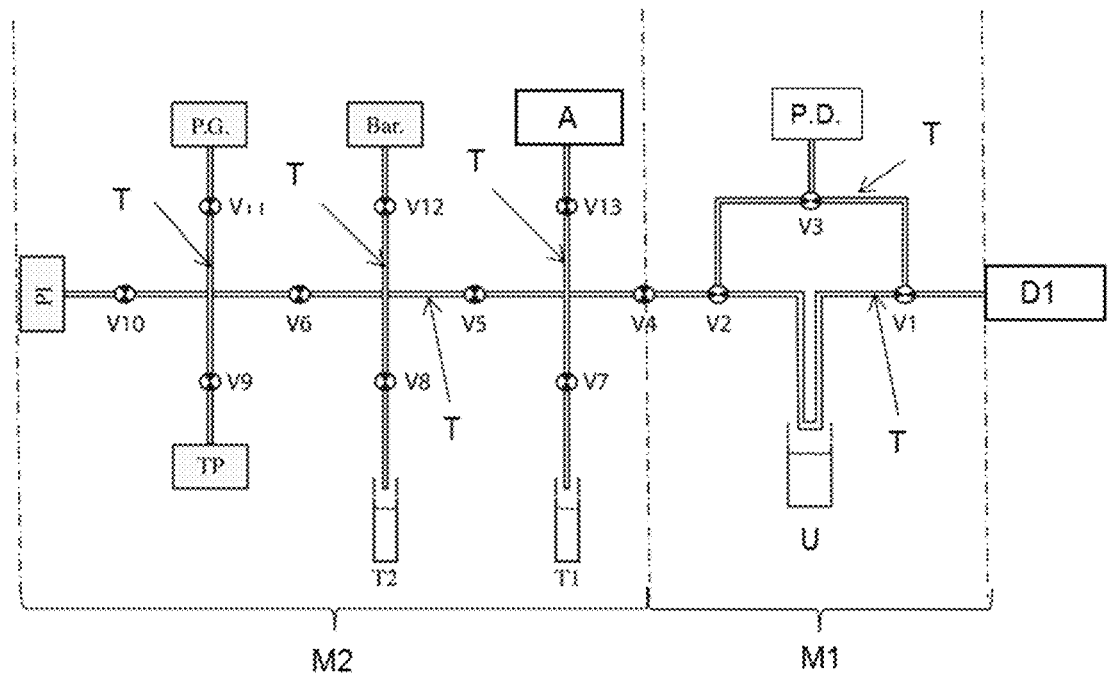
[Fig 2]
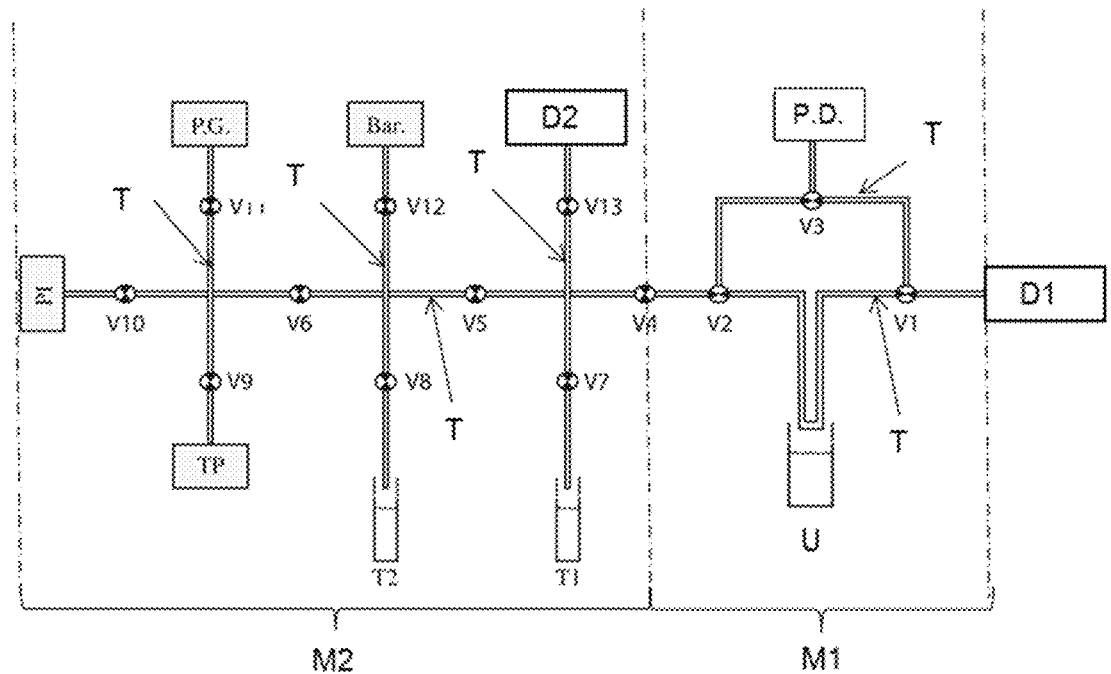

[Fig 3]
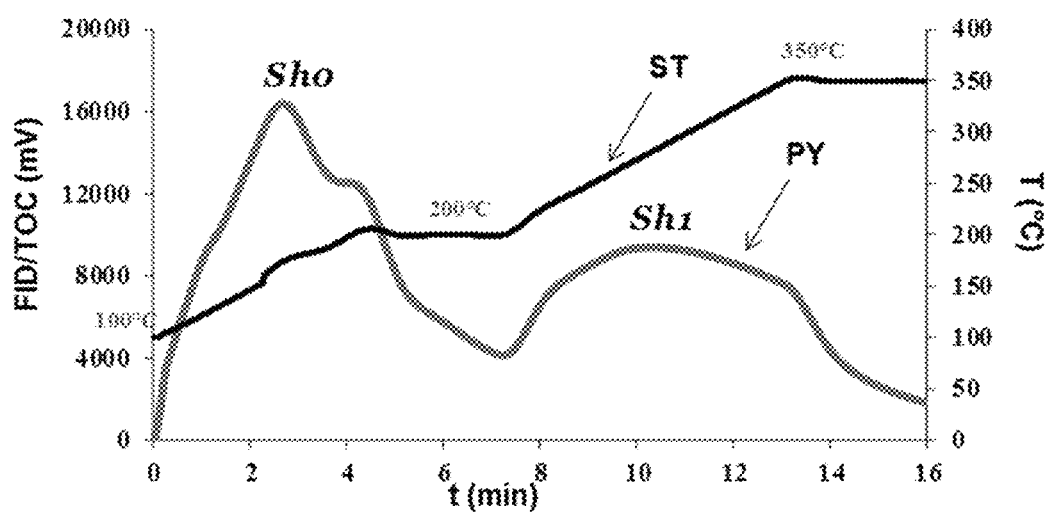
[Fig 4]
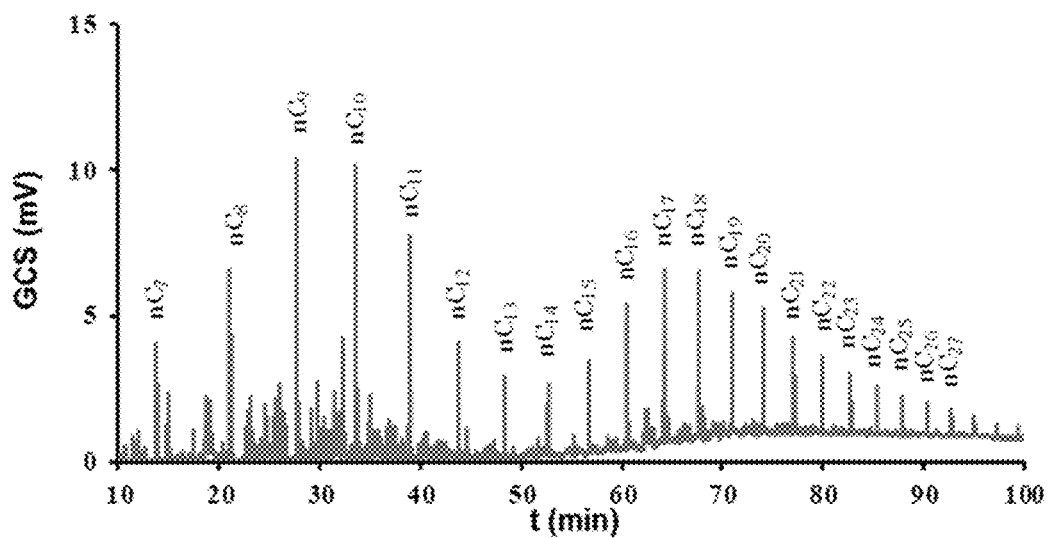

SYSTEM AND METHOD FOR DETERMINING THE CHEMICAL COMPOSITION OF COMPOUNDS CONTAINED IN A SAMPLE

CROSS-REFERENCE TO RELATED APPLICATION

Reference is made to French Patent Application No. 19/07.457, filed Jul. 4, 2019, the contents of which is incorporated herein by reference in its entirety.

BACKGROUND OF THE INVENTION

Field of the Invention

The present invention relates to the field of analysis of the chemical compounds of a sample in at least one gas, solid and liquid phase.

In particular, the present invention concerns, but is not limited to, the technical field of the oil industry, more specifically the field of exploration and development of a geological formation in which hydrocarbons are trapped. The present invention can determine the chemical composition of a rock sample from this formation, notably in order to precisely know the distribution among the heavy and light fractions of the hydrocarbon compounds contained in this sample. The present invention can further be supplemented by an analysis of other types of compounds, such as organosulfur compounds.

The present invention can also be advantageously implemented for environmental purposes, on a soil sample, so as to know the pollutant constituents thereof for example.

The present invention can however be implemented on any type of sample, such as oil, lubricant, carbonate rock sample, organic matter sample, organic fertilizer, at least one of an organic and an inorganic matrix, in order to precisely know the chemical composition thereof.

Description of the Prior Art

The ROCK-EVAL® device (IFP Energies nouvelles, France) developed by the applicant and notably described in patents FR-2,227, 797 corresponds to U.S. Pat. No. 3,953, 171 and FR-2,472,754 corresponding to U.S. Pat. No. 4,352, 673 is known. The ROCK-EVAL® device enables pyrolysis in an inert atmosphere (non-oxidizing), according to a predetermined sequence of temperatures, of a sample such as a sedimentary rock sample. The pyrolysis oven cooperates with a device for detecting and measuring the amount of hydrocarbon compounds in the pyrolyzed sample. The specific detection device comprises, for example, a flame ionization type detector (FID). The detector delivers a signal representative of the amounts of hydrocarbon products that are measured. This signal can be transmitted to a computation, storage and display wherein a specific software computes, displays and stores the various parameters representative of the characteristics of the hydrocarbons present.

The ROCK-EVAL® device further comprises an oxidation oven allowing obtaining information on the amount of total organic carbon (TOC), the amount of mineral carbon (MinC) or the amount of $SO_2$ relative to the sample being considered.

Thus, the ROCK-EVAL® device allows in particular measurement of the amount of hydrocarbon compounds released throughout pyrolysis. A pyrogram can then be established, which is a curve showing the evolution of the amount of released hydrocarbon compounds in relation to the weight of the sample being considered, as a function of time. A pyrogram generally has several peaks. See for example peaks Sh0 and Sh1 of FIG. 3, which are generally well differentiated. A quantity representative of the amount of hydrocarbon compounds released within the temperature range bounding the peak being considered is thus obtained from the surface area of one of these peaks.

The ROCK-EVAL® BULK ROCK method, which can be implemented by the ROCK-EVAL® device and is more particularly dedicated to conventional source rock samples, is also known. This method is notably described in the document (Behar et al., 2001). The sequence of temperatures of this method is characterized by an initial temperature T1 of the pyrolysis oven generally ranging between 300° C. and 350° C., a temperature that is maintained for a predetermined time duration of minutes. It is during this phase that the so-called "free" hydrocarbons (actually corresponding to low to high molecular weight hydrocarbons) initially contained in the rock sample are released. Their amount is estimated by measuring the surface area of a first peak, denoted by $S_1$. The pyrolysis temperature is then progressively raised to a temperature T2 of generally 650° C. This phase involves the volatilization of the very heavy hydrocarbon compounds and the cracking of the non-volatile organic matter (kerogen). The amount of hydrocarbon compounds released during this thermal cracking phase is assessed by measuring the surface area of a second peak, denoted by $S_2$. It corresponds to the amount of hydrocarbon compounds that would have been generated if the rock had reached a sufficient maturation stage.

The ROCK-EVAL® Reservoir method, which can also be implemented by the ROCK-EVA LC) device and is more particularly dedicated to reservoir rock and oil samples, is also known. This method is notably described in document EP-0,691,540 B1 corresponding to U.S. Pat. No. 5,843,787. The sequence of temperatures of the ROCK-EVA LC) Reservoir method is characterized by an initial temperature T1 of the pyrolysis oven below 200° C. and preferably equal to 180° C. This temperature is maintained for a predetermined time and the amount of light hydrocarbon compounds is assessed by measuring the surface area of a first peak, denoted by $S_{1r}$. The temperature of the pyrolysis oven is then raised to a second temperature T2 of about 370° C., a phase wherein the amount of heavier hydrocarbons released is estimated by assessing the surface area of a second peak, denoted by $S_{2a}$. Temperature T2 substantially corresponds to the end of the thermovaporization of some hydrocarbons and to the start of cracking through pyrolysis of the heavy compounds. Thus, the family of hydrocarbon compounds corresponding to peaks $S_{1r}$ and $S_{2a}$ of the Reservoir method is nearly equivalent to the family of hydrocarbon compounds characteristic of peak $S_1$ of the Basic method, that is light to heavy molecular weight hydrocarbons. The pyrolysis temperature is then increased again to a third temperature T3 of at most 650° C. The surface area of a third peak, denoted by $S_{2b}$, representative of the heavy hydrocarbon compounds, is estimated during this third heating phase. This peak $S_{2b}$ can be considered as an equivalent of peak $S_2$ of the ROCK-EVAL® BULK ROCK method.

The ROCK-EVAL® SHALEPLAY™ method has been developed more recently. It is notably described in patents FR 3,021,749 corresponding to US patent-10,088,465 and patent applications filed under number FR-17/59,447 corresponding to U.S. patent application Ser. No. 16/154,218), and it can also be implemented with of the ROCK-EVAL® device. These methods allow better quantification of the light to heavy hydrocarbons contained in a sedimentary rock, in particular an unconventional source rock, and more specifically to quantify the truly free light to heavy molecular weight hydrocarbon compounds and the amount of light to heavy molecular weight hydrocarbon compounds retained in the organic matter.

However, such analyses conducted by use of the ROCK-EVAL® device and of any one of the associated methods do not allow determination of the precise chemical composition of the sample being considered. An analytical methodology is therefore necessary to supplement the detection, recovery and quantification of chemical compounds obtained after an analysis conducted for example with the ROCK-EVAL® device.

Many analytical techniques have been developed in order to couple the pyrolysis of a sample with a direct online analysis such as, for example, with a gas chromatograph (GC) coupled with a flame ionization detector (FID) and with an isotope-ratio mass spectrometer (IRMS). The following document is notably known: Doerner, M., Berner, U., Erdmann, M. and Barth, T. (2017). *Paleoenvironmental Characterization of Thermally Mature Organic Matter Using a New Pyrolysis-IRMS method*, 28$^{th}$ International Meeting on Organic Geochemistry, 17-22 Sep. 2017, Florence, Italy, which combines a pyrolysis unit for heating a sedimentary rock sample according to a given sequence of temperatures with a GC/FID-IRMS analysis by trapping hydrocarbon fractions released by pyrolysis with a liquid nitrogen-cooled trap. However, the device described in this document does not enable separation, recovery and purification of fractions of compounds obtained at the pyrolysis unit outlet. Notably, as a result of the sequence of temperatures that is used, the hydrocarbons generated between 100° C. and 300° C. are not correctly separated (truncated peak S1 in FIG. 1 of document Doerner et al., 2017). Moreover, throughout the rest of the pyrolysis, different hydrocarbon fractions that are analysed seem to be arbitrarily separated every 25° C., without information on the composition of the hydrocarbons corresponding to these different fractions. Finally, the analysis performed in this document is destructive in the sense that the compound fractions obtained at the pyrolysis unit outlet are all used in the GC/FID-IRMS analysis, which does not allow performing additional, later and/or remote analyses.

SUMMARY OF THE INVENTION

The present invention is directed to overcoming these drawbacks.

The invention relates to a system and to a method for separating into at least one liquid and gas phases compounds contained in a sample, implemented by a first experimental setup for collecting the gas stream from a programmed pyrolysis according to a predetermined heating sequence and of a second vacuum experimental setup for separating and purifying at least one of the liquid and gas phases contained in this gas stream.

The invention further relates to a system and to a method for determining the chemical composition of compounds contained in a sample, implemented by use of at least one system for separating into at least one liquid and gas phases compounds contained in a sample as described above, which can be connected to any type of chemical composition analyzer arranged downstream, such as a gas chromatograph (GC), a gas chromatograph coupled with a mass spectrometer (GC-MS), and a gas chromatograph coupled with an isotope-ratio mass spectrometer (GC-IRMS), etc.

The invention relates to a system for separating into at least one liquid and gas phase compounds contained in a sample, comprising at least:

i. a first device comprising at least one oven for carrying out at least one heating sequence in an inert atmosphere according to a predetermined sequence of temperatures, apparatus (means) configured for separating into at least two parts an effluent resulting from the heating in an inert atmosphere, and apparatus (means) configured for continuous measurement of at least one amount of hydrocarbon compounds contained in the first part of the effluent;

ii. a first experimental setup configured for connection to the first device when the first device is in operation, comprising apparatus (means) configured for circulating the second part of the effluent from the first device towards means for collecting the second part of the effluent; and iii. a second experimental setup configured for connection to the first experimental setup when the first device is no longer in operation, comprising apparatus (means) comprising for vacuum circulation of the second part of the effluent collected by the first setup towards apparatus (means) configured for separating into at least one liquid and gas phase the collected second part of the effluent.

According to an implementation of the invention, the first device can further comprise an oxidation oven for heating in an oxidizing atmosphere.

According to an implementation of the invention, the means for circulating the second part of the effluent from the first device can include a pump and a flow meter.

According to an implementation of the invention, the means for circulating the second part of the effluent collected by the first setup can include a vacuum pump.

According to an implementation of the invention, the means for collecting the second part of the effluent can include a U-shaped tube cooled by a liquid nitrogen stream.

According to an implementation of the invention, the means for performing a separation into at least one liquid and gas phases can include two tubes cooled by a liquid nitrogen stream arranged in series in the direction of circulation of the second part of the effluent in the second setup, the tube located upstream containing at least a silica gel.

According to an implementation of the invention, at least one of the first and second experimental setups can include heating to avoid adsorption phenomena in the first and second setups, the temperature range of the heating means being between about 100° C. and 200° C.

According to an implementation of the invention, the second experimental setup can include apparatus (means) configured for collecting at least one of the separated liquid and/or gas phases.

According to an implementation of the invention, the system can comprise means for isolating respectively the first device and the first experimental setup, as well as the first experimental setup and the second experimental setup, with preferably the isolation means being valves, and more preferably multiway valves.

The invention further relates to a system for determining a chemical composition of compounds contained in a sample, comprising at least a system for separating into at least one liquid and gas phase compounds contained in a sample as described above and at least a second device configured for connection downstream from the second experimental setup, the second device being capable of analysing the chemical composition of the compounds contained in the at least one separated liquid and gas phase of the second part of the effluent.

According to an implementation of the invention, the second device can include at least one of a gas chromatograph and a gas chromatograph coupled with at least one of a mass spectrometer and a gas chromatograph coupled with an isotope-ratio mass spectrometer.

The invention further relates to a method for separating into at least one liquid and gas phase compounds contained in a sample, the method being implemented by use of a system as described above, wherein at least the following steps are carried out:

a. connecting the first device to the first experimental setup and heating the sample at least in an inert atmosphere according to a predetermined sequence of temperatures; separating continuously, during the heating in an inert atmosphere, into at least two parts an effluent resulting from the heating in an inert atmosphere; continuously measuring at least one amount of hydrocarbon compounds contained in the first part of the effluent and continuously collecting the second part of the effluent with the first experimental setup, b. disconnecting the first device from the first experimental setup and connecting the first setup to the second setup, and separating at least one of a liquid phase and a gas phase from the second part of the effluent with the second experimental setup.

The invention further relates to a method for determining a chemical composition of chemical compounds contained in a sample, the method being implemented by a system for determining a chemical composition of compounds contained in a sample as described above, wherein at least the steps of the method for separating at least one of liquid and gas phases compounds contained in a sample as described above are carried out, and wherein at least the following step is further carried out:

c. transferring at least one of the liquid and gas phases separated by the second experimental setup to the second device and determining the chemical composition of the compounds respectively contained in the liquid phase of the second part of at least one of effluent and in the gas phase of the second part of the effluent.

BRIEF DESCRIPTION OF THE FIGURES

FIG. 1 shows an example embodiment of the system according to the first aspect of the invention;

FIG. 2 shows an example embodiment of the system according to the second aspect of the invention;

FIG. 3 shows an example of a pyrogram obtained according to a predetermined sequence of temperatures; and FIG. 4 shows an example of a gas chromatogram obtained after implementing the method according to a third aspect of the invention.

DETAILED DESCRIPTION OF THE INVENTION

According to a first and a third aspect respectively, the invention relates to a system and to a method for separating into at least one liquid and gas phase compounds contained in any sample.

According to a second and a fourth aspect respectively, the invention relates to a system and to a method for determining the chemical composition of compounds contained in any sample, from at least one of the separated liquid and gas phases.

According to a first variant embodiment of the invention, the sample can come from a sedimentary rock of a subsoil formation comprising at least one of liquid and gaseous hydrocarbons. In this case, the system and the method according to the second and the fourth aspect of the invention can determine the chemical composition of at least the hydrocarbon compounds contained in the sample.

According to a second variant embodiment of the invention, the sample comes from at least one of organic and inorganic matrices such as, for example, recent sediments or soils, carbonates, fertilizers, etc.

According to a third variant embodiment of the invention, the sample is a petroleum product sample such as a lubricant or an oil. The system and the method according to the second and the fourth aspect of the invention can then determine the pollutant compounds contained in the sample, notably pollutants of organic compound type such as at least one of BTEX (Benzene Toluene Ethylbenzene) and the volatile organic compounds (VOC) that make up a very broad family of products found in gaseous form in the terrestrial atmosphere.

According to the invention, the sample can be at least one of liquid and solid. A sedimentary rock is an example of a solid sample comprising notably liquid ($>C_5$) and gaseous ($C_1$-$C_4$) hydrocarbon compounds if the sample is well preserved.

The system according to the first aspect of the invention comprises at least:

a) a first device comprising at least one oven for carrying out at least one heating sequence in an inert atmosphere according to a predetermined sequence of temperatures, apparatus (means) configured for separating into at least two parts an effluent resulting from the heating in an inert atmosphere, and apparatus (means) for continuous measurement of at least one amount of hydrocarbon compounds contained in the first part of the effluent, b) a first experimental setup configured connected to the first device when the first device is in service (i.e. in operation), comprising apparatus (means) for circulating the second part of the effluent from the first device towards apparatus (means) for collecting the second part of the effluent;

c) a second experimental setup configured connected to the first experimental setup when the first device is no longer in service (i.e. stopped after operation), comprising apparatus (means) for vacuum circulation of the second part of the effluent collected by the first setup towards means for separating into at least one of liquid and gas phases the collected second part of the effluent:

The system according to the second aspect of the invention further comprises a second device configured to be connected downstream from the second experimental setup of the system according to the first aspect of the invention, the second device being configured for performing an analysis of the chemical composition of the compounds contained in at least one of separated liquid and gas phases of the second part of the effluent.

The various elements of the system according to the first and the second aspect of the invention are described hereafter.

First Device (Heating Apparatus (Means))

The first experimental setup of the system according to at least one of the first and the second aspect of the invention comprises at least one oven for carrying out at least one heating sequence in an inert atmosphere according to a predetermined sequence of temperatures, apparatus (means) for separating into at least two parts an effluent from this heating sequence in an inert atmosphere, and apparatus (means) configured for continuously measuring at least one amount of hydrocarbon compounds contained in the first part of the effluent. Thus, the first device according to the invention performs at least one sequence of heating the sample being studied in an inert atmosphere for continuously measuring at least an amount of hydrocarbon compounds contained in the sample.

According to an implementation of the invention, the first device comprises means for programming heating of the oven according to the invention based on a predetermined sequence of temperatures.

According to an implementation of the invention, the sequence of temperatures can be the sequence of temperatures of the ROCK-EVAL® BULK ROCK method, as notably described in document (Behar et al., 2001), or the ROCK-EVAL® Reservoir method, as notably described in document EP 0,691,540 B1 corresponding to U.S. Pat. No. 5,843,787, or the ROCK-EVAL® SHALEPLAY™ method, as notably described in patents FR 3,021,749 corresponding to U.S. Pat. No. 10,088,465 and patent applications filed under number FR-17/59,447 corresponding to U.S. patent application Ser. No. 16/154,218, or any other heating sequence.

According to a preferred implementation of the invention, the predetermined heating sequence can be as follows:

a) from a first temperature value (T1) ranging between 50° C. and 120° C., raising the temperature of the sample according to a first temperature gradient ranging between 1° C./min and 50° C./min, up to a second temperature value (T2) ranging between 180° C. and 220° C., and maintaining the sample at the second temperature value (T2) for a predetermined time;

b) from the second temperature value (T2), raising the temperature of the sample according to a second temperature gradient ranging between 1° C./min and 50° C./min, up to a third temperature value (T3) ranging between 330° C. and 370° C., and maintaining the sample at the third temperature value (T3) for a second predetermined time.

This restricted version of the ROCK-EVAL® SHALEPLAY™ sequence of temperatures saves time in relation to the complete ROCK-EVAL® SHALEPLAY™ sequence of temperatures, while allowing release by thermovaporization of the lighter to heavy hydrocarbon compounds, which are the hydrocarbon compounds generally of interest.

According to an implementation of the invention, the apparatus (means) for providing continuous measurement of the hydrocarbon compounds released during pyrolysis can be a flame ionization detector (FID).

According to an implementation of the invention, the first device of the system according to at least one of the first and the second aspect of the invention can further allow heating in an oxidizing atmosphere. Heating in an oxidizing atmosphere can be done by an oven used for heating in an inert atmosphere according to the invention, which can operate in an inert atmosphere as well as in an oxidizing atmosphere, or by use of an oven separate from the oven used for heating in an inert atmosphere according to the invention. According to this implementation of the invention, the first device can further comprise:

apparatus (means) for continuously measuring an amount of $SO_2$ contained in the effluents after oxidation, such as an ultraviolet (UV) or an infrared (IR) spectrophotometer, apparatus (means) such as an infrared (IR) spectrophotometer for measuring the carbon monoxide (CO) and the carbon dioxide ($CO_2$) contained in the effluents after oxidation.

Preferably, the first device of the system according to at least one of the first and the second aspect of the invention corresponds to the ROCK-EVAL® device (IFP Energies nouvelles, France) developed by the applicant and notably described in patent EP-2,342,557 corresponding to U.S. Pat. No. 8,796,035.

First Experimental Setup (Effluent Circulation and Collection Apparatus (Means))

The first experimental setup of the system according to at least one of the first and the second aspect of the invention comprises apparatus (means) for circulating the second part of the effluent, coming from the first device according to the invention, apparatus (towards) means for collecting this second part of the effluent.

Furthermore, according to the invention, this first experimental setup is intended to be connected to the first device according to the invention when the first device is in operation. According to an implementation of the invention, the system can comprise apparatus (means) for isolating the first device and the first experimental setup. Preferably, the isolation apparatus (means) can be valves, and more preferably multiway valves. Thus, this first experimental setup is mounted "online" when the first device is in operation.

According to an implementation of the invention, the apparatus (means) for collecting the second part of the effluent from the first device according to the invention can include a liquid nitrogen-cooled U-trap tube.

According to an implementation of the invention, the apparatus (means) for circulating the second part of the effluent coming from the first device towards the collection apparatus (means) of the first experimental setup can further include a pump, a flow meter and at least one 3-way valve.

According to an implementation of the invention, the carrier gas used in the first experimental setup can be an inert gas such as nitrogen.

Advantageously, the first experimental setup can further include heating apparatus (means) to avoid adsorption phenomena in the various elements of the first experimental setup. According to an implementation of the invention, the temperature range of the heating means can be between about 100° C. and 200° C., and the temperature is preferably 150° C. According to an implementation of the invention, the heating apparatus (means) can be heating cords.

According to an implementation of the invention, the first experimental setup can further include one or more stainless steel tubes (marketed by the Swagelok company, USA, for example), ¼ inch (about 6.35 mm) in diameter for example, through which the second part of the effluent coming from the first device according to the invention circulates.

Second Experimental Setup (Vacuum Circulation Apparatus (Means) for the Collected Effluent)

The second experimental setup according to the invention comprises apparatus (means) for vacuum circulation of the second part of the effluent collected by the first experimental setup towards apparatus (means) for performing separation into at least one liquid and gas phases of the second part of the collected effluent. Vacuum circulation allows avoiding contamination by air and thus provides a precise quantitative balance.

Furthermore, according to the invention, this second experimental setup is configured to be connected to the first experimental setup when the first device of the system according to at least one of the first and the second aspect of the invention is no longer in operation. According to an implementation of the invention, the system can include apparatus (means) for isolating the first experimental setup and the second experimental setup. Preferably, the isolation can be by valves, and more preferably multiway valves. The second experimental setup is thus mounted "offline" in relation to the first device according to the invention.

Advantageously, the system comprises apparatus (means) for respectively isolating the first device and the first experimental setup, as well as the first experimental setup and the second experimental setup, preferably, the isolation apparatus (means) are valves, and more preferably multiway valves.

According to an implementation of the invention, the apparatus (means) for performing separation into at least one of liquid and gas phases of the second part of the collected effluent can include two liquid nitrogen-cooled tubes arranged in series in the direction of circulation of the second part of the effluent in the second setup, the upstream tube (in relation to the direction of circulation of the second part of the collected effluent circulating in the second experimental setup) containing at least a silica gel. Silica gel is notably capable of trapping gases such as methane for example.

According to an implementation of the invention, the means intended for vacuum circulation of the second part of the effluent collected by the first setup towards the means for separating the part into at least one of liquid and gas phases can include at least one vacuum pump.

Advantageously, the second experimental setup can further include heating apparatus (means) to avoid adsorption phenomena in the second experimental setup. According to an implementation of the invention, the temperature range of the heating apparatus (means) can be between about 100° C. and 200° C., and the temperature is preferably 150° C. According to an implementation of the invention, the heating apparatus (means) of the second experimental setup can be heating cords.

According to an implementation of the invention, the second experimental setup can further include one or more stainless steel tubes (marketed by the Swagelok company, USA, for example), ¼ inch (about 6.35 mm) in diameter for example, through which the second part of the effluent circulates after collection by the first experimental setup of the system according to the first or the second aspect of the invention.

Thus, the second experimental setup of the system according to the first or the second aspect of the invention enables vacuum separation of at least one of the liquid and gas phases contained in the second part of the effluent obtained by using the first device according to the invention and collected by the first experimental setup according to the invention.

Advantageously, the system according to the first aspect of the invention can further include apparatus (means) for collecting at least one of the liquid and gas phases thus separated, for example by means of funnels (made of glass for example) that may be connected for example through one or more stainless steel tubes (marketed by the Swagelok company, USA, for example, ¼ inch (about 6.35 mm) in diameter for example) and one or more multiway valves to the apparatus (means) for separation into at least one liquid and gas phases of the second experimental setup (such as the tubes cooled by a liquid nitrogen stream according to the implementation of the invention described above).

Second Device (Chemical Composition Analysis Apparatus (Means)

The system according to the second aspect of the invention further comprises at least a second device intended to be connected downstream from the second experimental setup according to any one of the above variants. The second device is capable of analysing the chemical composition of the compounds contained in the separated at least one liquid and gas phases of the second part of the effluent.

According to an implementation of the system according to the second aspect of the invention, the second device can correspond to a gas chromatograph (GC), which obtains the various compounds of a sample.

Alternatively or combinedly, the second device of the system according to the second aspect of the invention can correspond to a gas chromatograph (GC) coupled with a mass spectrometer (GC-MS), which enables detection and identification of the compounds according to their mass-to-charge ratio.

Alternatively or combinedly, the second device of the system according to the second aspect of the invention can correspond to a gas chromatograph (GC) coupled with an isotope-ratio mass spectrometer (GC-IRMS), which allows measuring the relative abundance of the various isotopes of a single chemical element in a given sample.

According to an implementation of the second aspect of the system according to the invention, the second device can be directly connected to the second experimental setup for example through one or more stainless steel tubes (for example the tubes marketed by the Swagelok company, USA, ¼ inch (about 6.35 mm) in diameter for example) and one or more multiway valves.

Alternatively, the system according to the second aspect of the invention can further be automated transfer of at least one of the liquid and gas phases from the second experimental setup to the second device.

According to a third aspect, the invention relates to a method for separating at least one of the liquid and gas phases of the compounds contained in a sample, and the method can be implemented by using a system for separating at least one of the liquid and gas phases of a sample according to any one of the embodiments of the first or the second aspect of the invention described above.

The method for separating at least one of the liquid and gas phases of compounds contained in a sample according to the invention comprises at least the following steps:

a) heating of the sample at least in an inert atmosphere and performing collection of the liquid and gas phases, b) separating the liquid and gas phases.

According to a fourth aspect, the invention relates to a method for determining the chemical composition of compounds contained in a sample, and the method can be implemented by use of the system for determining the chemical composition of compounds contained in a sample according to any one of the embodiments of the second aspect of the invention described above. The method for determining the chemical composition of compounds contained in a sample (fourth aspect) comprises carrying out at least steps a) and b) of the method for separating at least one of the liquid and gas phases of the compounds of a sample according to any one of the variants described hereafter, and at least an additional step c) of analysing the chemical compounds of at least one of the liquid and gas phases from step b).

The steps of the methods according to at least one of the third and the fourth aspect of the invention are described hereafter.

a) Heating of the Sample at Least in an Inert Atmosphere and Collection

In this step, the first device of the system according to at least one of the first and the second aspect of the invention is connected to the first experimental setup and the sample is heated at least in an inert atmosphere according to a predetermined sequence of temperatures. Then, in a continuous manner while heating in an inert atmosphere, an effluent resulting from heating in an inert atmosphere is separated into at least two parts. At least one amount of hydrocarbon compounds contained in the first part of the effluent is then continuously measured and the second part of the effluent is continuously collected by use of the first experimental setup.

According to an implementation of the invention, the predetermined sequence of temperatures can be the sequence of temperatures of the ROCK-EVAL® BULK ROCK method, as notably described in document (Behar et al., 2001), or the ROCK-EVAL® Reservoir method, as notably described in document EP 0,691,540 B1 corresponding to U.S. Pat. No. 5,843,787, or the ROCK-EVAL® SHALEPLAY™ method, as notably described in patents FR 3,021,749 corresponding to U.S. Pat. No. 10,088,465 and patent applications filed under number FR 17/59,447 corresponding to U.S. patent application Ser. No. 16/154,218, or any other heating sequence.

According to a preferred implementation wherein the first device of the system according to the invention is a ROCK-EVAL® device, the stream of hydrocarbon compound gas released by the heating sequence in an inert atmosphere is divided into two parts. A first part that is sent to a flame ionization detector (FID) of the ROCK-EVAL® device, and a second part is sent to the first experimental setup of the system according to the invention, in order to be collected for example in a liquid nitrogen-cooled U-trap tube.

According to an implementation of the invention, this step can extend over a period ranging between 10 minutes and 40 minutes, and it preferably lasts 25 minutes. Such durations ensure that the majority of at least one of the thermovaporizable and pyrolyzable chemical compounds contained in the sample being considered has been released, then collected.

Advantageously, during this performed collection phase using the first experimental setup, at least part of the elements of the first experimental setup (more precisely, at least except for the element dedicated to collecting the effluent, such as the U-trap tube in the preferred embodiment of the first experimental setup) is maintained at a temperature ranging between 100° C. and 200° C., preferably 150° C., by heating cords for example. This allows avoiding adsorption of the compounds released by the first device on the walls of the elements of the first experimental setup (except for the element dedicated to effluent collection, such as the U-trap tube in the preferred embodiment of the first experimental setup).

b) Separation into at Least One of Liquid and Gas Phases

In this step, the first device of the first experimental setup of the system according to at least one of the first and the second aspects of the invention is disconnected and the first experimental setup is connected to the second experimental setup of the system according to at least one of the first and the second aspects of the invention.

Advantageously, this can be achieved by isolating at least one of the first and the second experimental setup, and these isolations can be performed valves, which are preferably multiway valves.

At least one of a liquid phase and a gas phase of the second part of the effluent is then separated by the second experimental setup of the system according to at least one of the first and the second aspect of the invention, which comprises at least vacuum circulation of the second part of the effluent collected by the first setup towards the separation of an effluent into at least one of liquid and gas phases.

According to a preferred embodiment of the system according to the invention, the second experimental setup of the system according to at least one of the first and the second aspect of the invention can comprise two tubes cooled by a liquid nitrogen stream (the liquid nitrogen stream is applied outside the two tubes). According to this implementation, the tubes are arranged in series in the direction of circulation of the stream generated by the circulation of the second experimental setup, the upstream tube (in relation to the direction of circulation of the stream generated by the circulation of the second experimental setup) contains at least silica gel. Silica gel is notably capable of trapping gases such as methane for example. Thus, the gas phase of the second part of the effluent is first collected in the first tube of the second experimental setup, located upstream in relation to the direction of circulation, then the liquid phase of the second part of the effluent is collected in the second tube located downstream in relation to the direction of circulation.

According to an implementation of the invention, this step can extend over a period ranging between 5 minutes and 30 minutes, and it preferably lasts 15 minutes, to stabilize in each of the two tubes of the second experimental setup.

Advantageously, during vacuum circulation of the second part of the effluent in the second experimental setup, at least part of the elements of the second experimental setup (more precisely, at least except for the element dedicated to collecting the separated at least one of gas and liquid phases) can be maintained at a temperature ranging between 100° C. and 200° C., preferably 150° C., by use of heating cords for example. This avoids adsorption of the compounds present in the second part of the effluent on the walls of the various elements of the second experimental setup (except for those dedicated to collecting the gas and liquid phases once separated). According to the preferred implementation of the system according to at least one of the first and the second aspects of the invention wherein the second experiment setup comprises two liquid nitrogen-cooled tubes, that may however have not been maintained at a temperature ranging between 100° C. and 200° C. during this phase of vacuum circulation of this second part of the effluent.

Advantageously, when at least one of the liquid and gas phases of the second effluent have been separated (i.e. after about 15 minutes), vacuum circulation can be stopped in the second experimental setup and at least one of the liquid and gas phases thus separated are collected.

According to the preferred implementation of the system according to one of the aspects of the invention wherein the second experimental set comprises two liquid nitrogen-cooled tubes, the content of the two tubes can be transferred for collecting at least one of the liquid and separated gas phases (such as funnels for example, notably made of glass), through one or more stainless steel tubes (for example the tubes marketed by the Swagelok company, USA, ¼ inch (about 6.35 mm) in diameter for example) and one or more multiway valves. Advantageously, this phase of collecting at least one of the liquid and gas phases can be accelerated by heating these two tubes to a temperature ranging between 100° C. and 200° C., preferably 150° C., by heating cords for example.

c) Analysis of the Chemical Compounds of the Liquid and/or Gas Phases

This step is carried out within the context of the method for determining the chemical composition of the compounds contained in a sample (fourth aspect of the invention).

In this step, at least one of the liquid and gas phases separated by the second experimental setup are transferred to the second device of the system in order to determine the chemical composition of the compounds contained in a sample (second aspect of the invention), and the chemical composition of the compounds respectively contained in at least one of the liquid phase of the second part of the effluent and in the gas phase of the second part of the effluent is determined.

Advantageously, when at least one of the liquid and gas phases of the second effluent have been separated (i.e. after about 15 minutes), vacuum circulation can be stopped in the second experimental setup and the collected liquid and gas phases can be transferred to the second device of the system according to the invention.

According to the preferred implementation of the system according to the invention wherein the second experimental setup comprises two liquid nitrogen-cooled tubes, the content of the two tubes is transferred to the second device of the system according to the invention, for example by heating the two tubes to a temperature ranging between 100° C. and 200° C., preferably 150° C., by use of heating cords for example.

The hydrocarbon compounds released by heating the sample at least in an inert atmosphere by use of the first device, are trapped by the first experimental setup, then separated into at least one of liquid and gas phases by the second experimental setup, can then be analysed using a gas chromatograph (GC or GC-FID), a gas chromatograph coupled with a mass spectrometer (GC-MS), a gas chromatograph coupled with an isotope-ratio mass spectrometer (GC-IRMS), or any other analyzer.

FIG. 1 shows a non-limitative example embodiment of the system according to the first aspect of the invention, comprising:

i. a first device D1, which is preferably a ROCK-EVAL® device as described above, ii. a first experimental setup M1, referred to as "online" setup. According to this implementation of the invention, the first experimental setup has: a stainless steel Swagelok tube T with a U-trap, stainless steel Swagelok tubes T with three 3-way ball valves V1, V2 and V3, a pump associated with a flow meter P.D., and heating cords (not shown). Valve V1 allows connection to first device D1, iii. a second experimental setup M2, referred to as "offline" setup. This second setup has stainless steel Swagelok tubes T (with Swagelok unions, crosses and tees, fittings and connections made of stainless steel), valves V4 to V13 of VCR type with Swagelok leak-tight seals, two stainless steel tube traps (T1 and T2 containing silica gel), two pumps—a primary pump PI and a secondary turbopump TP—, a vacuum gauge P.G. of Pfeiffer-1 type, a manometer Bar. of Baratron-1 type and heating cords (not shown). This second setup, offline, under vacuum, provides purification and separation, if necessary, of the gaseous compounds from the liquid compounds. This implementation of the system according to the first aspect of the invention also comprises a funnel A for collecting for example at least one of the gas separated phase and the liquid phase.

FIG. 2 shows a non-limitative example embodiment of the system according to the second aspect of the invention, comprising a device D1 and experimental setups M1 and M2 as described above for the embodiment of the system according to the first aspect of the invention, except that collector funnel A is replaced by a device D2 capable of analysing the chemical composition of the compounds contained in at least one of liquid and gas phases, such as a gas chromatograph for example.

A non-limitative example of implementation of the method according to the third aspect of the invention is described hereafter, which is achieved by the system according to the first aspect of the invention with one embodiment of being shown in FIG. 1 (notably the references mentioned are those of FIG. 1):

i. A pyrolysis is carried out in an inert atmosphere according to the heating sequence of the restricted ROCK-EVAL® SHALEPLAY™ method, as in the preferred embodiment described above, on the sample to be analysed by device D1 of ROCK-EVAL® type as described above. During this analysis, the stream of hydrocarbon compound gas is separated into two parts. One part is sent to a flame ionization detector of the ROCK-EVAL® device and the other is sent to the first experimental setup M1 coupled with the ROCK-EVAL® device D1. Concurrently with the heating sequence carried out in an inert atmosphere by the ROCK-EVAL® device D1, a continuous nitrogen stream is applied in first experimental setup M1 coupled with ROCK-EVAL® device D1 during the operating phase of ROCK-EVAL® device D1. This continuous nitrogen stream is provided by pump P.D. associated with a flow meter. The compounds at least one of thermovaporized and pyrolyzed for example) sent to first experimental setup M1 flow through the trap. In order to trap all the hydrocarbon compounds, this U-trap is cooled by the temperature of the liquid nitrogen without trapping the carrier gas circulating in first experimental setup M1. The pumping associated with the ROCK-EVAL® device can remain operational in order to complete the desired at least one of the pyrolysis and oxidation cycle, and thus to supplement the analysis of the sample, ii. When the temperature program of the ROCK-EVAL® device D1 is completed, the U-trap is isolated from the ROCK-EVAL® device using valve V1. Then the U-trap is connected to second experimental setup M2 by valves V2 and V4. When the U-trap is connected to second experimental setup M2, the part of first experimental setup M1 connected to second experimental setup M2 is heated to about 150° C.+/−50° C. The previously trapped compounds are released and transferred into the circuit of second experimental setup M2, and notably in the two tubes T1 and T2 cooled to the temperature of the liquid nitrogen. Tube T1 contains silica gel for trapping methane. After a stabilization time (about 15 minutes), the compounds trapped in these tubes T1 and T2 are isolated from the rest of second experimental setup M2 using valves V7 and V8. The rest of the line is subjected to pumping using pumps PI and TP. The whole line, except for the two cold trap tubes T1 and T2, can be heated by heating cords to about 150° C.+/−50° C. to prevent compound loss due to adsorption on the stainless steel tubes, iii. Finally, in order to recover the hydrocarbon compounds, pumping is stopped, and trap tubes T1 and T2 are reconnected to the line using valves V7 and/or V8, to recover only the methane or all the hydrocarbons. Traps T1 and T2 are then heated to accelerate the release of hydrocarbons, by heating cords. After a stabilization time (about 15 minutes), funnel A for collecting one of the phases, gas or liquid, is isolated by valve V13 and removed, possibly to continue the analyses, for example by gas chromatography, or any other analysis.

Thus, the methods and systems according to the invention allow trapping of the effluents of a pyrolysis performed in a nitrogen stream, then to purification and concentration of these effluents by pumping the carrier gas and other potential contaminants prior to feeding the effluents of interest into the second experimental setup under vacuum.

The method and the system for separating the compounds of a sample into liquid gas phases enables non-destructive analysis by keeping at least one of the liquid and gas phases thus separated (in glass funnels for example), with a view to one or more additional, later and remote analyses. Indeed, at the end of the method according to the third aspect of the invention, all of the at least one of liquid and gas phases thus collected can be used for a single analysis, or at least one of the liquid and gas phases thus collected can be divided so as to perform different types of analyses (using for example a gas chromatograph, a gas chromatograph coupled with a mass spectrometer, a gas chromatograph coupled with an isotope-ratio mass spectrometer) allowing reaching additional conclusions for example. The method and the system for separating the compounds of a sample into at least one of the liquid and gas phases according to the invention are also particularly advantageous in the case of chemical composition analyses that could not be directly performed after collection, due to at least one of the long analysis time and to an equipment present in external laboratories.

The systems according to the first and the second aspect of the invention can be implemented by any type of pyrolysis unit. The system according to the second aspect of the invention can generally be used by any type of device capable of analysing the chemical composition of the compounds contained in the at least one liquid and gas phases. Thus, the systems according to the invention enable great flexibility.

EXAMPLES

The advantages of the methods and the systems according to the invention are presented hereafter.

The method according to the third aspect of the invention has been applied to an oil sample, by use of the embodiment of the system according to the first aspect of the invention described above in connection with FIG. 1. The content of the liquid phase in funnel A has then been collected and transferred for gas chromatography analysis.

FIG. 3 shows a pyrogram PY representative of the FID/TOC signal (signal measured by a FID detector, normalized relative to the total organic carbon) from an analysis performed by the ROCK-EVAL® device according to the preferred heating sequence ST, in the present case the restricted ROCK-EVAL® SHALEPLAY™ sequence, as described above in the preferred embodiment and illustrated in FIG. 3.

This figure shows:

a first peak Sh0 corresponding to the hydrocarbon compounds released during the first heating ramp (between 100° C. and 200° C.) and the first plateau (at 200° C.) of the preferred heating sequence ST, a second peak Sh1 corresponding to the hydrocarbon compounds released during the second heating ramp (between 200° C. and 350° C.) and the second plateau (at 350° C.) of the preferred heating sequence ST.

In general, such a pyrogram represents the amount of hydrocarbon compounds released over time by thermovaporization, according to the selected heating sequence. In particular, the surface area of peak Sh0 (given for example in milligram of hydrocarbon compound per gram of rock) is representative of the amount of lighter thermovaporizable hydrocarbons (whose number of carbon atoms is below 20) contained in the sample considered. The surface area of peak Sh1 (given for example in milligram of hydrocarbon compound per gram of rock) is representative of the heavier thermovaporizable hydrocarbons (whose number of carbon atoms ranges between 20 and 30).

FIG. 4 shows a gas chromatogram obtained after analysing the content of funnel A into which only the liquid phase present in tube T2 has been transferred. A gas chromatogram is obtained using a gas chromatograph (GC) allowing detection and separation of molecules of a mixture. This information is therefore a complement to pyrogram PY obtained at the end of the heating sequence performed at least in an inert atmosphere. In particular, analysis of the chromatogram allows concluding on the types of hydrocarbon compounds contained in the liquid phase. Notably, the joint analysis of FIGS. 3 and 4 allows concluding that, among the lighter compounds contributing to peak Sh0 of the pyrogram, there are very few hydrocarbon compounds having a number of carbon atoms below 7 (first significant peak of the chromatogram corresponding to the hydrocarbon compounds having a number of carbon atoms equal to 7, denoted by nC7 in FIG. 4).

Thus, the implementation of the method according to the third aspect of the invention, supplemented with an analysis of the chemical composition of the compounds contained in the at least one of separated liquid and gas phases, allows quantitative and qualitative characterization of the organic compounds released by pyrolysis. Furthermore, when the system according to the invention comprises means for collecting at least one of the liquid and gas phases thus separated (such as a funnel), the at least one of the liquid and gas phases thus separated can be kept for one or more later analyses, for example using at least one of a gas chromatograph, a gas chromatograph coupled with a mass spectrometer and a gas chromatograph coupled with an isotope-ratio mass spectrometer. Furthermore, these devices can be remote devices.

The invention claimed is:

1. A system for separating into at least one of liquid and gas phases compounds contained in a sample, comprising:
   i. a first device comprising at least one oven for carrying out at least one heating sequence in an inert atmosphere according to a predetermined sequence of temperatures, means for separating into at least two parts an effluent resulting from the heating in an inert atmosphere, and means for continuous measurement of at least one amount of hydrocarbon compounds contained in a first part of the effluent;
   ii. a first experimental setup configured to be connected to the first device when the first device is in operation, comprising means for circulating a second part of the effluent from the first device towards means for collecting the second part of the effluent; and
   iii. a second experimental setup configured to be connected to the first experimental setup when the first device is no longer in operation, comprising means for providing vacuum circulation of the second part of the effluent collected by the first experimental setup towards means configured for separating the collected second part of the effluent into at least one of liquid and gas phase.

2. A system for separating as recited in claim 1, wherein the first device further comprises an oxidation oven for heating in an oxidizing atmosphere.

3. A system for separating as claimed in claim 1, wherein, in the first experimental setup, the means for circulating the second part of the effluent from the first device includes a pump and a flow meter.

4. A system for separating as claimed in claim 2, wherein, in the first experimental setup, the means for circulating the second part of the effluent from the first device includes a pump and a flow meter.

5. A system for separating as claimed in claim 1 wherein, in the second experimental setup, the means for circulating the second part of the effluent collected by the first experimental setup includes a vacuum pump.

6. A system for separating as claimed in claim 1 wherein, in the first experimental setup, the means for collecting the second part of the effluent includes a U-shaped tube cooled by a liquid nitrogen stream.

7. A system for separating as claimed in claim 1 wherein, in the second experimental setup, the means for performing a separation into at least one liquid and gas phase includes two tubes cooled by a liquid nitrogen stream in series in a direction of circulation of the second part of the effluent in the second experimental setup, with the tube being located upstream and containing at least a silica gel.

8. A system for separating into at least one of liquid and gas phases compounds contained in a sample as claimed in claim 1, wherein at least one of the first and second experimental setups include a heater for avoiding adsorption phenomena in the first and second experimental setups with the temperature range of heating of the heater being between about 100° C. and 200° C.

9. A system for separating into at least one of liquid and gas phases compounds contained in a sample as claimed in claim 1, wherein the second experimental setup includes means for collecting the separated at least one of the liquid and gas phases.

10. A system for separating into at least one of liquid and gas phases compounds contained in a sample as claimed in claim 1, wherein the system comprises means for isolating respectively a first experimental device and a first experimental setup, a first experimental setup and a second experimental setup, and the means for isolating comprises multiway valves.

11. A method for separating into at least one liquid and gas phase compounds contained in a sample, the method being implemented by use of the system as claimed in claim 1, wherein the following steps are carried out:
  a. connecting the first device to the first experimental setup and heating the sample at least in an inert atmosphere according to a predetermined sequence of temperatures; separating continuously, during the heating in an inert atmosphere, into at least two parts an effluent resulting from the heating in an inert atmosphere; continuously measuring at least one amount of hydrocarbon compounds contained in the first part of the effluent and continuously collecting the second part of the effluent by the first experimental setup; and
  b. disconnecting the first device from the first experimental setup and connecting the first setup to the second setup, and separating at least one of a liquid phase and a gas phase from the second part of the effluent with the second experimental setup.

12. A method for determining a chemical composition of chemical compounds contained in a sample, the method being implemented by use of the system as claimed in claim 11, wherein at least the steps of the method for separating into at least one liquid and gas phase compounds contained in a sample are carried out, and wherein at least a further step is carried out:
  transferring at least one of the liquid and the gas phase separated by the second experimental setup to the second device and determining the chemical composition of the compounds contained in at least one liquid phase of the second part of the effluent and in the gas phase of the second part of the effluent.

13. A system for determining a chemical composition of compounds contained in a sample, comprising at least a system for separating into at least one liquid and gas phase compounds contained in a sample as claimed in claim 1 and at least a second device configured for connection downstream from the second experimental setup, the second device being configured for analysing the chemical composition of the compounds contained in the separated at least one liquid and gas phase of the second part of the effluent.

14. A system for determining a chemical composition of compounds contained in a sample as claimed in claim 13, wherein the second device includes at least one of a gas chromatograph, a gas chromatograph coupled with a mass spectrometer, and a gas chromatograph coupled with an isotope-ratio mass spectrometer.

15. A method for determining a chemical composition of chemical compounds contained in a sample, the method being implemented by use of the system as claimed in claim 13, wherein at least the steps of the method for separating into at least one liquid and gas phase compounds contained in a sample are carried out, and wherein at least a further step is carried out:
  c. transferring the at least one of the liquid and the gas phase separated by the second experimental setup to the second device and determining the chemical composition of the compounds contained in the at least one of the liquid phase of the second part of the effluent and in the gas phase of the second part of the effluent.

* * * * *